United States Patent [19]

Rayudu

[11] Patent Number: 5,023,332
[45] Date of Patent: Jun. 11, 1991

[54] 1-METHYL-3,5,7-TRIAZA-1-AZONIATRICYCLODECANE TRIIODIDE

[75] Inventor: S. Rao Rayudu, Germantown, Tenn.

[73] Assignee: Buckman Laboratories International, Inc., Memphis, Tenn.

[21] Appl. No.: 427,364

[22] Filed: Oct. 27, 1989

Related U.S. Application Data

[62] Division of Ser. No. 268,205, Nov. 4, 1988, Pat. No. 4,892,583.

[51] Int. Cl.$^5$ ............................................ C07D 487/18
[52] U.S. Cl. .................................................... 544/185
[58] Field of Search ................................ 544/185, 186

[56] References Cited

U.S. PATENT DOCUMENTS

| | | | |
|---|---|---|---|
| 4,505,831 | 3/1985 | Fenyes | 252/34 |
| 4,650,866 | 3/1987 | Rayudu | 544/186 |
| 4,920,107 | 4/1990 | Pera | 514/244 |

*Primary Examiner*—John M. Ford
*Attorney, Agent, or Firm*—Finnegan, Henderson, Farabow, Garrett & Dunner

[57] ABSTRACT

A method of preserving an aqueous system which is susceptible to microbiological degradation, comprising the step of adding to the system a compound having the formula

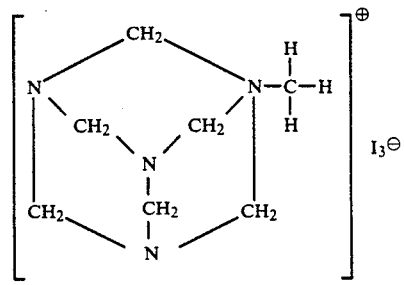

wherein the compound is added in an amount sufficient to inhibit the growth and proliferation of at least one microorganism in the aqueous system.

The compound 1-methyl-3,5,7-triaza-1-azoniatricyclodecane triiodide and a method for preparing same comprising the substitution of triiodide anion for a monohalide anion in an aqueous medium.

1 Claim, No Drawings

1-METHYL-3,5,7-TRIAZA-1-AZONIATRICYCLO-DECANE TRIIODIDE

This is a division of application Ser. No. 268,205, filed Nov. 4, 1988, now U.S. Pat. No. 4,892,583.

FIELD OF THE INVENTION

The present invention relates to a method for the preservation of aqueous systems which are susceptible to microbiological degradation through the use of 1-methyl-3,5,7-triaza-1-azoniatricyclodecane triiodide. Typical systems include aqueous solutions, emulsions and suspensions.

The present invention also relates to the novel compound 1-methyl-3,5,7-triaza-1-azoniatricyclodecane triiodide and a method for its preparation.

BACKGROUND OF THE INVENTION

A large number of commercial and industrial products comprise aqueous systems containing organic materials. Examples are latexes, surfactants, dispersants, stabilizers, lubricants, thickeners, adhesives, starches, waxes, proteins, emulsifying agents, detergents, cellulose products, and resins formulated in aqueous solutions, emulsions or suspensions. Such products frequently contain relatively large amounts of water. The temperature at which these products are stored, as well as their pH, makes these products susceptible to the growth of microorganisms. These microorganisms can be introduced during the manufacturing of these products (from exposure to air, tanks, pipes, equipment, and humans), and/or during their use (from multiple openings and reclosures of packaged products, and introduction of contaminated objects to stir or remove material).

Microbiological degradation of aqueous systems containing organic material may manifest itself in a variety of problems. These include loss of viscosity, gas formation, objectionable odors, decreased pH, emulsion breaking, color change, and gelling.

Friedrich et al., Zur Kenntnis des Hexamethylentetramins, I., 54B Berichte 1531–42 (1921), discloses 1-methyl-3,5,7-triaza-1-azoniatricyclodecane compounds which include anions such as methyl sulfate, nitrate, picrate, perchlorate, and thiocyanate groups. Pending U.S. Pat. applications No. 174,812 and 174,819 additionally disclose anions of acetate, citrate, borate, phosphate and molybdate.

U.S. Pat. Nos. 4,505,831 and 4,650,866 disclose 1-methyl-3,5,7-triaza-1-azoniatricyclodecane compounds, useful as microbicides. These patents, however, are limited to such compounds having monohalide anions. U.S. Pat. No. 4,650,866 also discloses a method for preparing such 1-methyl-3,5,7-triaza-1-azoniatricyclodecane halides comprising the reaction of an ammonium halide with methylamine, formaldehyde and ammonia in an aqueous medium.

DESCRIPTION OF THE INVENTION

The present invention provides a method for the preservation of an aqueous system which is susceptible to microbiological degradation, comprising the step of adding to the system a compound having the formula

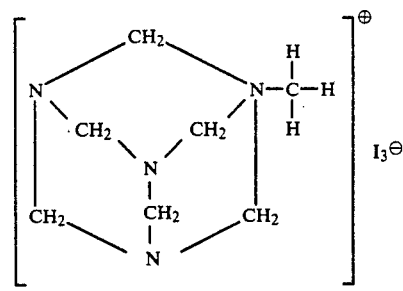

wherein the compound is added in an amount sufficient to inhibit the growth and proliferation of at least one microorganism in the aqueous system.

The present invention also provides a method for preparing the compound of the invention comprising substituting a triiodide ion for a monohalide anion in the compounds disclosed in U.S. Pat. No. 4,650,866, incorporated herein by reference, preferably 1-methyl-3,5,7-triaza-1-azoniatricyclodecane chloride. A triiodide solution may be prepared by mixing iodine and an alkali metal iodide, preferably sodium or potassium iodide, in water. The monohalide compound is added, and the compound of the present invention is obtained. All of the starting materials for this process are readily available commercial products.

In the method of preparation of the present invention, the triiodide solution is preferably prepared at a strength of 0.01 to 0.1 molar concentration in water, more preferably approximately 0.05 molar. This solution may be prepared by dissolving 0.01 to 0.1 moles iodine and 0.02 to 0.20 or more moles alkali metal iodide per liter of water. The preferred ratio is 0.05 moles iodine to 0.12 moles iodide per liter of water.

The process of preparation is preferably conducted at ambient room temperatures. It is not an exothermic reaction.

The reaction is conducted for a time sufficient to prepare the triiodide salt of the present invention. Preferably, the reaction is conducted for about one hour to four hours.

The method of this invention may be used to prevent microbiological degradation in any aqueous system susceptible to such degradation, such as aqueous solutions, emulsions and suspensions.

Examples of aqueous solutions, emulsions, and suspensions which are subject to microbiological degradation include water-based paints, latex emulsions, such as acrylic and polyvinyl acetate emulsions, adhesive solutions and emulsions, wax emulsions, polishes, metalworking fluid solutions and emulsions, caulking and sealant products, papermaking chemical products such as alum solutions, clay and pigment dispersions, starch slurries and solutions, and protein coating formulations, and cosmetic preparations. Many of these materials are also used in other industrial and commercial products. Aqueous systems may be used in petroleum production and in the manufacture of detergents, surfactants, inks and textiles.

A particularly preferred use of the compound of the present invention is in the preservation of water-based paints.

The antimicrobial activity of the compound used in accordance with the invention extends to a variety of different microorganisms, including bacteria such as

*Escherichia coli, Staphylococcus aureus, Pseudomonas aeruginosa, Enterobacter aerogenes, Klebsiella pneumoniae, Proteus vulgaris, Salmonella choleraesuis* and *Bacillus subtilis,* and fungi such as *Candida albicans* and *Aspergillus niger.*

The concentration of the compound of this invention which inhibits growth and proliferation of a microorganism, and thus provides the preservative effect described herein, may be readily determined by one skilled in the art without extensive experimentation and, preferably, will range from about 25 parts to about 5000 parts by weight of the compound for one million parts of the aqueous system to be preserved.

This invention also relates to the novel compound 1-methyl-3,5,7-triaza-1-azoniatricyclodecane triiodide.

The compound of the invention may be utilized as a solid or may be dissolved in water prior to addition to the product being preserved. In those instances wherein the presence of water might cause some degradation of the quaternary ammonium salt over a long period of time, non-aqueous dispersions could be prepared by the proper selection of solvents, dispersants, and stabilizers which are well-known in the art as being suitable for the formation of such dispersions.

In those instances wherein the compound of the invention is subject to rapid degradation by heat, stabilizers may be added.

To illustrate the nature of the invention, the following examples are given. It should be understood, however, that the invention is not to be limited to the specific conditions or details set forth in these examples.

EXAMPLE 1

Preparation of
1-Methyl-3,5,7-triaza-1-azoniatricyclodecane triiodide

A solution of 12.7 g (0.05 moles) of iodine, 20 g (0.12 moles) of potassium iodide, and 1 liter of water was prepared in a 2 liter beaker. To the above well-stirred solution was slowly added 54 g of 18% solution of 1-methyl-3,5,7-triaza-1-azoniatricyclodecane chloride (0.05 moles). During the addition of the organic chloride to the triiodide solution, a brown solid precipitated. This was filtered and dried to yield 11.7 g (44.5% yield) of a brown solid with a melting point of 160°-162° C. Elemental analysis of this showed this to be fairly pure:

TABLE 1

| Element | % Calc. | % Found | % Found |
|---|---|---|---|
| C | 15.67 | 15.28 | 15.43 |
| H | 2.80 | 2.71 | 2.66 |
| I | 71.08 | 72.48 | 72.54 |
| N | 10.45 | 10.15 | 10.16 |

EXAMPLE 2

The preservative effectiveness of the quaternary ammonium triiodide prepared in Example 1 was determined in a freshly prepared water-based paint formulated with titanium dioxide and calcium carbonate as pigments, an acrylic emulsion resin, dispersants, and hydroxyethyl cellulose as thickener. The pH of this paint was approximately 9.0. A multiple challenge procedure used was as follows:

A. Weigh 100 g. of paint into prenumbered French square bottles.

B. Add the appropriate amount of the preservative to obtain the desired parts per million.

C. Add 1 ml. of inoculum. Mix well by shaking the contents of each bottle immediately after the addition of the inoculum. The inoculum was prepared by adding 2 ml. of sterile saline solution to an 18- to 24-hr. agar culture of *Enterobacter aerogenes,* agitating to loosen the surface growth, and decanting to a sterile test tube. The procedure was repeated with cultures of *Pseudomonas aeruginosa* and *Bacillus subtilis,* and all three suspensions were decanted to the same test tube. The concentration of the mixed bacterial suspension was then adjusted so that a final concentration of $1 \times 10^5$ cells per ml. is achieved when one ml. of the inoculum is added to 100 ml. of the paint.

D. Include a minimum of two controls (bottles containing substrate and inoculum only).

E. Incubate at 37° C. for 9 weeks.

F. Streak from the contents of each bottle onto nutrient agar plates at intervals of 3 days, 7 days, 14 days, and 21 days after inoculating (first challenge). Incubate the streaked plates at 37° C. for 24 hours and observe the streaked plates for growth.

G. Reinoculate the test with the same test organisms at the end of 21 days and streak from the contents of each bottle onto nutrient agar plates at intervals of 3 days, 7 days, 14 days and 21 days after inoculating (second challenge). Incubate the streaked plates at 37° C. for 24 hours and observe the streaked plates for growth.

H. Reinoculate the test with the same test organisms at the end of 42 days and streak from the contents of each bottle onto nutrient agar plates at intervals at 3 days, 7 days, 14 days and 21 days after incoulating (third challenge). Incubate the streaked plates at 37° C. for 24 hours and observe the streaked plates for growth.

I. Observe the contents of each bottle for
 1. Color change
 2. Odor
 3. Thickening of paint J. Evaluate the results. A chemical is considered an effective preservative when it prevents the growth of bacteria 21 days after each inoculation.

The quaternary ammonium triiodide described in Example 1 wa an effective preservative at concentrations of 400 parts of the salt per one million parts of paint and also at higher concentrations. See Table 2 below. No color changes were noted in any of the tests. In addition, no undesirable odors were observed and the viscosities of the preserved paint samples did not change.

TABLE 2

| Concentration (ppm) | Observation of Growth | | | | | | | | | | | |
|---|---|---|---|---|---|---|---|---|---|---|---|---|
| | 1st Challenge | | | | 2nd Challenge | | | | 3rd Challenge | | | |
| | 3 | 7 | 14 | 21 | 3 | 7 | 14 | 21 | 3 | 7 | 14 | 21 |
| 100 | ++ | ++ | ++ | ++ | ++ | ++ | ++ | ++ | * | ++ | ++ | ++ |
| 250 | 0 | 0 | ++ | ++ | ++ | ++ | ++ | ++ | ++ | ++ | ++ | ++ |
| 400 | 0 | 0 | 0 | 0 | ++ | 0 | 0 | 0 | 0 | 0 | 0 | 0 |
| 500 | + | 0 | 0 | 0 | + | 0 | 0 | 0 | 0 | 0 | 0 | 0 |
| 1000 | 0 | 0 | 0 | 0 | 0 | 0 | 0 | 0 | 0 | 0 | 0 | 0 |

TABLE 2-continued

| Concentration | Observation of Growth | | | | | | | | | | | |
|---|---|---|---|---|---|---|---|---|---|---|---|---|
| | 1st Challenge | | | | 2nd Challenge | | | | 3rd Challenge | | | |
| (ppm) | 3 | 7 | 14 | 21 | 3 | 7 | 14 | 21 | 3 | 7 | 14 | 21 |
| 3000 | 0 | 0 | 0 | 0 | 0 | 0 | 0 | 0 | | 0 | 0 | 0 |

\* No samples were taken at this time point.
Key:
0 = No colonies
+ = 1 to 10 colonies
++ = More than 10 colonies

We claim:

1. The compound 1-methyl-3,5,7-triaza-1-azoniatricyclodecane triiodide.

* * * * *

Disclaimer 5,023,332—*S. Rao Rayudu*, Germantown, Tenn. 1-METHYL-3,5,7-TRIAZA-1-AZONIATRICYCLODECANE TRIIODIDE. Patent dated June 11, 1991. Disclaimer filed May 21, 1992, by the assignee, Buckman Laboratories International, Inc.

Hereby enters this disclaimer to claim 1 of said patent.